US012561831B2

(12) United States Patent
Sun et al.

(10) Patent No.: US 12,561,831 B2
(45) Date of Patent: Feb. 24, 2026

(54) DYNAMIC POSITION RECOGNITION AND PROMPT SYSTEM AND METHOD

(71) Applicant: Jedicare Medical Co., Ltd., Shanghai (CN)

(72) Inventors: Fei Sun, Shanghai (CN); Yi Zhu, Shanghai (CN); Xiaojie Guo, Shanghai (CN); Fuli Cui, Shanghai (CN); Ying Shan, Shanghai (CN)

(73) Assignee: Jedicare Medical Co., Ltd., Shanghai (CN)

( * ) Notice: Subject to any disclaimer, the term of this patent is extended or adjusted under 35 U.S.C. 154(b) by 190 days.

(21) Appl. No.: 18/553,351

(22) PCT Filed: Mar. 18, 2022

(86) PCT No.: PCT/CN2022/081729
§ 371 (c)(1),
(2) Date: Sep. 29, 2023

(87) PCT Pub. No.: WO2022/206436
PCT Pub. Date: Oct. 6, 2022

(65) Prior Publication Data
US 2024/0185448 A1 Jun. 6, 2024

(30) Foreign Application Priority Data
Apr. 1, 2021 (CN) .......................... 202110358154.8

(51) Int. Cl.
*G06T 7/70* (2017.01)
*A61B 90/00* (2016.01)
(Continued)

(52) U.S. Cl.
CPC ................ *G06T 7/70* (2017.01); *A61B 90/37* (2016.02); *G06T 7/50* (2017.01); *G06T 11/00* (2013.01);
(Continued)

(58) Field of Classification Search
CPC ................................. G06T 19/20; G06F 3/017
(Continued)

(56) References Cited

U.S. PATENT DOCUMENTS

2013/0208005 A1    8/2013    Kasahara et al.
2014/0081659 A1    3/2014    Nawana et al.
(Continued)

FOREIGN PATENT DOCUMENTS

CN    103458219 A    12/2013
CN    108319274 A    7/2018
(Continued)

OTHER PUBLICATIONS

International Search Report issued for International Application No. PCT/CN2022/081729, entitled "Dynamic Position Identification and Prompt System and Method," mailed on May 25, 2022.

*Primary Examiner* — Samantha (Yuehan) Wang
(74) *Attorney, Agent, or Firm* — Hamilton, Brook, Smith & Reynolds, P.C.

(57) ABSTRACT

A dynamic position recognition and prompt method and system. The system comprises: a recognition module (1), a judgment module (2) and a prompt module (3); wherein the recognition module (1) is used to obtain a current scene image via an image obtaining device and recognize a current position of a specific object in the current scene image; the judgment module (2) is used to judge whether the current position of the specific object is within a preset recognition range; the prompt module (3) is used to performing navigation for the specific object if the current position of the specific object is not within the preset recognition range of the image obtaining device, to help a user in finding the specific object to be in the predetermined recognition range, so that the image and the navigation are more accurate and precise.

11 Claims, 3 Drawing Sheets

(51) Int. Cl.
*G06T 7/50* (2017.01)
*G06T 11/00* (2006.01)

(52) U.S. Cl.
CPC .................. *A61B 2090/365* (2016.02); *G06T 2207/10028* (2013.01); *G06T 2207/30004* (2013.01)

(58) Field of Classification Search
USPC ......................................................... 345/629
See application file for complete search history.

(56) References Cited

U.S. PATENT DOCUMENTS

| | | | |
|---|---|---|---|
| 2015/0282796 A1 | 10/2015 | Nawana et al. | |
| 2017/0172696 A1 | 6/2017 | Saget et al. | |
| 2017/0367771 A1 | 12/2017 | Tako et al. | |
| 2018/0210627 A1* | 7/2018 | Woo ........................ | G06F 3/012 |
| 2019/0053855 A1 | 2/2019 | Siemionow et al. | |
| 2019/0231443 A1 | 8/2019 | Mcginley et al. | |
| 2020/0085511 A1 | 3/2020 | Oezbek et al. | |
| 2022/0211444 A1* | 7/2022 | Dassonville ........... | A61B 34/20 |
| 2024/0000432 A1* | 1/2024 | Usuda ................... | A61B 8/463 |

FOREIGN PATENT DOCUMENTS

| | | |
|---|---|---|
| CN | 111595349 A | 8/2020 |
| CN | 113509265 A | 10/2021 |
| WO | 2020/231654 A1 | 11/2020 |

* cited by examiner

Specific Object

Recognition Feature

Image Obtaining Device

Preset Recognition Range

The Second Circle

The First Circle

FIG. 6

DYNAMIC POSITION RECOGNITION AND PROMPT SYSTEM AND METHOD

This application is the U.S. National Stage of International Application No. PCT/CN2022/081729, filed Mar. 18, 2023, which designates the U.S., published in Chinese, and claims priority under 35 U.S.C. § 119 or 365(c) to Chinese Application No. 202110358154.8, filed Apr. 1, 2021. The entire teachings of the above applications are incorporated herein by reference.

TECHNICAL FIELD

The present invention relates to the field of image processing technology, and in particular to a dynamic position recognition and prompt system and method.

BACKGROUND

When an image obtaining device recognizes the position of an object, due to the limitations of the algorithms, positioning accuracy may change dynamically as the distance between a recognized object and the image obtaining device varies. For example, if the recognized object is far away from the image obtaining device, the number of feature points that are available for recognition significantly decreases, thereby affecting positioning accuracy. In another example, if the recognized object is very close to the image obtaining device, the image may be distorted due to lens distortion at different positions, thereby causing a decrease in positioning accuracy. This phenomenon results in that a specific area in front of the image obtaining device is the optimal range for recognizing and positioning surgical instruments. How to make it intuitive and convenient for an operator to keep the recognizable instruments within the range and to ensure that positioning accuracy is continuously conformity with design expectations is one of the difficulties in implementation of augmented reality navigation technology.

For example, in augmented reality-based navigation technology for puncture surgery, since an optical image obtaining device used to obtain position information of the recognized object is worn on the operator's head, and the operator needs to hold a puncture device recognizable for the image obtaining device and operate it to perform different surgical actions, the distance between the image obtaining device and the recognized object changes dynamically at any time, which in turn affects the operations in the surgical process.

SUMMARY

For the above defects or problems, it is an object of the present invention to provide a dynamic position recognition and prompt system and method thereof.

In order to achieve the above purpose, the technical solution of the present invention is as follows.

A dynamic position recognition and prompt system comprises: a recognition module, a judgment module, and a prompt module; wherein, the recognition module is used to obtain a current scene image via an image obtaining device, and recognize a current position of a specific object in the current scene image;

the judgment module is used to judge whether the current position of the specific object is within a preset recognition range;

the prompt module is used to display a prompt message in an augmented reality manner to prompt a user to adjust the specific object to be within the preset recognition range if the current position of the specific object is not within the preset recognition range.

The preset recognition range is a recognition distance range and/or a recognition angle range which is preset; the judgment module is specifically used to judge whether the specific object is within the recognition distance range; and/or to judge whether the specific object is within the recognition angle range.

The preset recognition range is set to be a spatial shape range radially increasing along a shooting direction of the image obtaining device.

The judgment module comprises an optimal recognition range judgment sub-module for judging whether the current position of the specific object is within the optimal recognition range of the image obtaining device; the optimal recognition range is within the preset recognition range, and the preset recognition range is greater than the optimal recognition range.

The judgment module further comprises a recognition range setting module for setting the preset recognition range and/or the optimal recognition range.

The optimal recognition range comprises: an optimal recognition range preset based on the user's instruction and/or a historical optimal recognition range obtained based on data statistics.

The prompt module is further used to display the prompt message in the augmented reality manner. The prompt message comprises at least a positional relationship between the specific object and the preset recognition range to prompt the user to adjust the position of the specific object or the image obtaining device.

The prompt message is one or a combination of more of text, color, pattern, and animation superimposed on the current scene in the augmented reality manner.

The prompt module further comprises a movement prompt sub-module for displaying a position movement message to prompt the user to move the position of the specific object or the image obtaining device, so that the specific object is enabled to be within the preset recognition range. The position movement message comprising: one or a combination of more of text, auxiliary line, or animation superimposed on the current scene in the augmented reality manner.

The specific object is a specific object with a recognizable feature.

A dynamic position recognition and prompt method comprises:

obtaining a current scene image;

recognizing a current position of a specific object in the current scene image;

judging whether the current position of the specific object is within a preset recognition range;

displaying a prompt message in an augmented reality manner to prompt a user to adjust the specific object to be within the preset recognition range if the current position of the specific object is not within the preset recognition range.

The preset recognition range is a recognition distant range and/or a recognition angle range which is preset;

Said judging whether the current position of the specific object is within the preset recognition range comprises:

judging whether the specific object is within the recognition distance range; and/or judging whether the specific object is within the recognition angle range.

The preset recognition range is set to be a spatial shape range radially increasing along a shooting direction of the image obtaining device.

The method further comprises judging whether the current position of the specific object is within an optimal recognition range of the image obtaining device; the optimal recognition range is within the preset recognition range, and the preset recognition range is greater than the optimal recognition range.

The optimal recognition range is adjusted according to the operation requirement. When the specific object is in a fine operation requirement, the optimal recognition range contracts; and when the specific object is in a rough operation requirement, the optimal recognition range expands.

The optimal recognition range comprises: an optimal recognition range preset based on the user's instruction and/or a historical optimal recognition range obtained based on data statistics.

The prompt message comprises at least a positional relationship between the specific object and the preset recognition range to prompt the user to adjust the position of the specific object or the image obtaining device.

The prompt message is one or a combination of more of text, color, pattern, and animation superimposed on the current scene in the augmented reality manner.

Said displaying the prompt message in the augmented reality manner to prompt the user to adjust the specific object to be within the preset recognition range comprises: displaying a position movement message to prompt the user to move the position of the specific object or the image obtaining device, so that the specific object is enabled to be within the preset recognition range. The position movement message comprises: one or a combination of more of text, auxiliary line, or animation superimposed on the current scene in the augmented reality manner.

The specific object is a specific object with a recognizable feature.

In comparison with the prior art, the beneficial effects of the present invention are as follows.

The present invention provides the dynamic position recognition and prompt system and method thereof. By determining of the position of the specific object in the obtained scene in real time, the relation between the current position of the specific object and the preset recognition range is determined, and then the positional relationship adjustment information is displayed in the augmented reality manner for the specific object to prompt the user to move the position of the specific object or the image obtaining device, so as to achieve the purpose that the positional relationship between the specific object and the image obtaining device is in the preset recognition range. The present invention can navigate the specific object and help the user to enable the specific object to be in the preset recognition range. For example, in the augmented reality navigation technology for puncture surgery, it can ensure that the user can quickly and accurately locate the medical device and master this skill.

In addition, the present invention is also capable of defining a three-dimensional optimal recognition range and a three-dimensional optimal recognition angle relative to the image obtaining device according to the expected positioning accuracy. By calculating in real time the relative relationship between the current position of the specific object and the optimal recognition area, the operator is prompted by means of color, graphics, animation, etc., whether the recognition position should be adjusted at present, and that the specific object is adjusted to a suitable position, so that the subsequent surgical steps can be continued.

BRIEF DESCRIPTION OF THE DRAWINGS

FIG. 6 is a diagram of an angle prompt in the preset recognition range in the dynamic position recognition and prompt method of the present invention.

DETAILED DESCRIPTION

The present invention will be described in detail in the following in conjunction with the drawings, and it is obvious that the described embodiments are only a part but not all of the embodiments of the present invention. Based on the embodiments of the present invention, all other embodiments obtained by those of ordinary skill in the art without making creative work are within the protection scope of the present invention.

In performing some clinical surgeries, especially in scenes where accurate operations are carried out, it is required to obtained surgical scene images by an image obtaining device, and then position and recognize the surgical device in the scene, so that a user is able to conduct surgical navigation for the entire surgical process by means of displayed augmented reality images, and in turn perform surgical operations on a patient to achieve the purpose of treating the patient; for the entire navigation and positioning process, the surgical device needs to be within a preset recognition range at all times, and it is necessary to continuously confirm whether the navigated device is continually within an optimal recognition area during the surgical process. Training alone cannot ensure that the operator can quickly and accurately master this skill. Therefore, a continuous interactive optimal recognition range prompt method becomes necessary. The setting of the preset recognition range usually needs to be based on the position of the image obtaining device. In some embodiments, where the image obtaining device is placed at a fixed position in the surgical scene to capture images of the scene in real time to recognize the position of the surgical device, the preset recognition range is at a fixed position relative to the surgical scene. In other embodiments, the image obtaining device is not fixed, for example, where an image obtaining device on a head-mounted device worn by an operator is utilized to capture image of the scene in real time to recognize the position of the surgical device, the preset recognition range is fixed relative to the location of the image obtaining device, but is not fixed relative to the surgical scene.

Taking a surgical implementation scene as an example, the present invention provides a user with positioning of a handheld machine. Wherein, the user is an observer of the entire navigation process, also an operator who probes the handheld machine into the body of the target. The target may be a person or other animal on which the user needs to operate. The specific object in the present invention is a handheld machine, for example a medical device with a recognition feature. The medical device may be any tool that can be probed into the body of the target, for example: a puncture needle, a biopsy needle, a radiofrequency or microwave ablation needle, an ultrasound probe, a rigid endoscope, an oval forceps for endoscopic surgery, an electrotome, an anastomosis, and the like.

Figure 1:
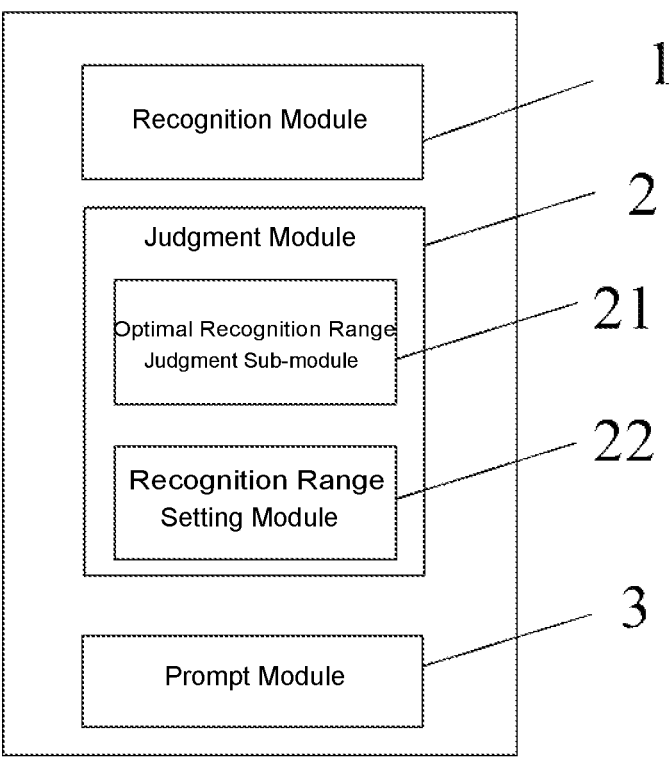
FIG. 1 is a structural diagram of a dynamic position recognition and prompt system of the present invention.

As shown in FIG. 1, the present invention also provides a dynamic position recognition and prompt system, which comprises: a recognition module 1, a judgment module 2, and a prompt module 3; wherein the recognition module 1 is used to obtain a current scene image via an image obtaining device, and recognize a current position of a specific object in the current scene image;

the judgment module 2 is used to judge whether the current position of the specific object is within a preset recognition range;

the prompt module 3 is used to display a prompt message in an augmented reality manner to prompt a user to adjust the specific object to be within the preset recognition range if the current position of the specific object is not within the preset recognition range.

In the present invention, the preset recognition range is a recognition distance range and/or a recognition angle range which is preset; the judgment module 2 is specifically used to judge whether the specific object is within the recognition distance range; and/or to judge whether the specific object is within the recognition angle range.

Wherein, the preset recognition range is set to be a spatial shape range radially increasing along a shooting direction of the image obtaining device, comprising: a spatial shape, with the image obtaining device as a proximal end, radially increasing along an image obtaining direction toward a distal end. Exemplarily, the spatial shape is a conical structure.

The judgment module 2 further comprises an optimal recognition range judgment sub-module 21 for judging whether the current position of the specific object is within an optimal recognition range of the image obtaining device; the optimal recognition range being within the preset recognition range, the preset recognition range being greater than the optimal recognition range.

The judgment module further comprises a recognition range setting module 22 for setting the preset recognition range and/or the optimal recognition range. Preferably, the optimal recognition range comprises: an optimal recognition range preset based on the user's instructions and/or a historical optimal recognition range obtained based on data statistics.

Wherein, the prompt module is further used to display a prompt message in the augmented reality manner, the prompt message comprising at least a positional relationship between the specific object and the preset recognition range to prompt the user to adjust the position of the specific object or the image obtaining device. The prompt message is one or a combination of more of text, color, pattern and animation superimposed on the current scene in the augmented reality manner.

The prompt module further comprises a movement prompt sub-module for displaying a position movement message to prompt the user to move the position of the specific object or the image obtaining device, so that the current positon of the specific object is within the preset recognition range; the position movement message comprising: one or any combination of more of text, auxiliary line or animation superimposed on the current scene in the augmented reality manner.

It is to be noted that the specific object of the present invention is a specific object with a recognizable feature. For example, the specific object is a surgical device with a recognition feature. In the present invention, the surgical device can be recognized and positioned by means of the recognition feature.

Figure 2:
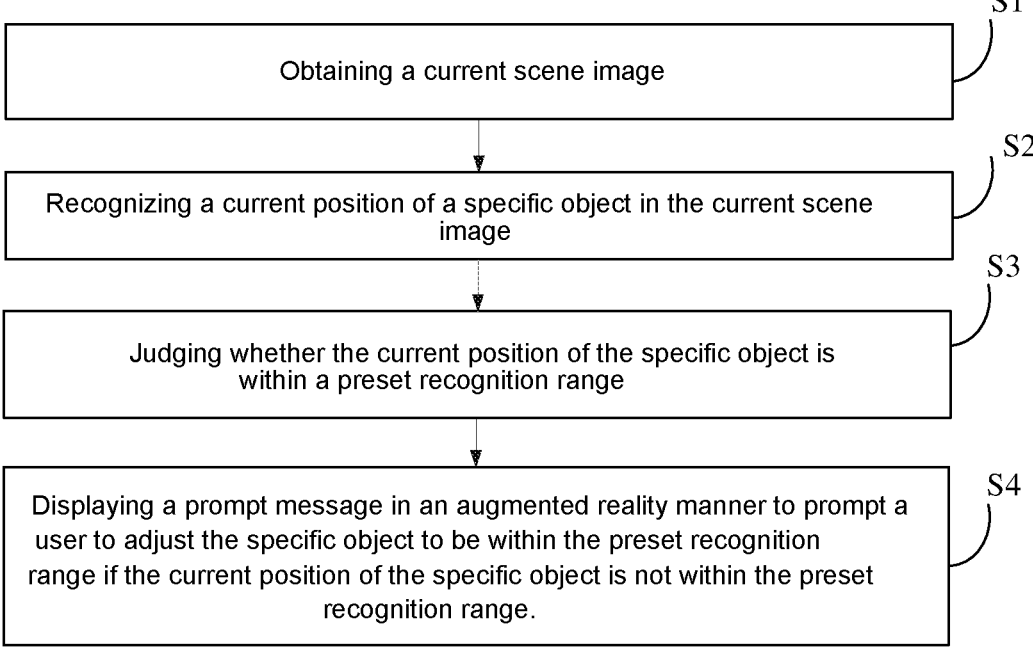
FIG. 2 is a flowchart of a dynamic position recognition and prompt method of the present invention.

In addition, as shown in FIG. 2, the present invention further provides a dynamic position recognition and prompt method, comprising:

In S1, a current scene image is obtained.

In a specific surgical scene, a surgical device is required to perform operations. The specific object is a movable medical device as described above, which is disposed a recognition feature that can be recognized. The recognition feature comprises at least an object body morphological characteristic and/or an object marker recognition feature. The object body morphological characteristic comprises at least the structure, the form, or the color of the object body, and the object marker recognition feature comprises at least a pattern, a graphic, or a two-dimensional code disposed on the second object. For example, the two-dimensional code is a black-and-white planar graphic distributed on a plane, the points on which are very easy to recognize, and by recognizing at least three of the points, the two-dimensional code can be positioned. Since the two-dimensional code is fixed to a target or a device, the target or the device fixed with the two-dimensional code can be positioned. Optionally, the object marker recognition feature may also be other planar graphics such as a chessboard pattern. Using the two-dimensional code or the chessboard pattern as an identifier makes the positioning of the target or the device more accurate and faster. This allows for more accurate navigation of the fast moving device. However, in specific implementations, it is not limited to these features, but can also be other features of the object that can be recognized.

Optionally, the identifier fixed on the surface of the medical device may also be a three-dimensional graphic. For example, in the process of design and production of the device, the graphic of the identifier may be the handle of the device, or a certain structure fixed to the side of the handle. Spatial position using three-dimensional graphic has higher accuracy for stationary or slow-moving targets, although the computational time required for recognition is relatively long compared to that of planar graphic.

In S2, the current position of the specific object in the current scene image is recognized.

Figure 3:
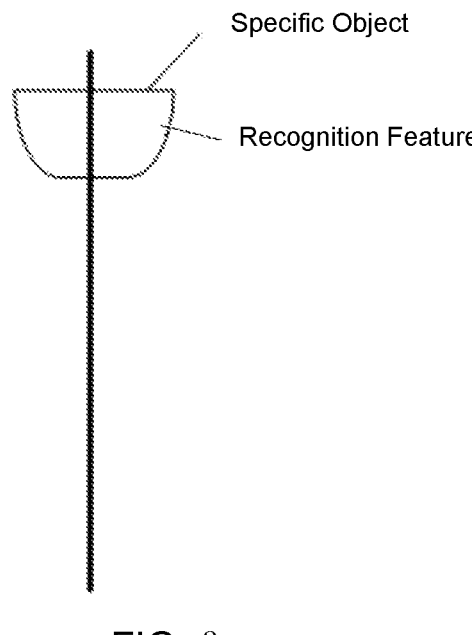
FIG. 3 is a specific structure diagram of a specific object in the dynamic position recognition and prompt method of the present invention.

Exemplarily, the specific object of the present invention is a surgical device with a recognition feature. In an embodiment, as shown in FIG. 3, the specific object is a puncture needle using during a surgery process. An end of the puncture needle is disposed with a bowl-shaped structure which is easily recognizable, and a two-dimensional code is printed on the surface of the bowl-shaped structure. In the process of surgical operation, the user holds the puncture needle to perform surgery on the target, and it is required to obtain the current scene image via the image obtaining device, and then to recognize the position of multiple feature points on the two-dimensional code according to the current scene image to obtain the current position of the surgical device within the scene by the system. However, the surgical device constantly moves during the entire process, thus during the surgical process, the surgical device is not always at a static position. In the process of moving, the surgical device is not always within the ideal positional range, thereby affecting the effect of the entire surgical process, especially for those users who are not very skilled, resulting in operational difficulties. Therefore, in the present invention, the surgical device can be recognized during the surgery by means of the recognition feature, and the position of the surgical device can be obtained in real time.

In S3, it is judged whether the current position of the specific object is within the preset recognition range.

Since during the entire operation process, the specific object is not always within the positional region range where it can be easily shot and recognized, and this problem cannot be found in real time, thus the user's operation process is monitored and recognized in real time by means of the technical means in the present invention.

Specifically, the preset recognition range is a recognition distance range and/or a recognition angle range which is preset; the judgment module is specifically used to judge whether the specific object is within the recognition distance range; and/or to judge whether the specific object is within the recognition angle range.

In the embodiment, the image obtaining device is a device capable of obtaining images. In some embodiments, the image obtaining device may be an image obtaining device on the head-mounted device worn by the user with the shooting angle being aligned with the user's observation direction. Optionally, the image obtaining device is a head-mounted optical image obtaining device. The device not only ensures that the shooting angle is the observation angle of the user, ensuring the accuracy, but also avoids the interference with various operations of the user during use, thereby significantly improving the user experience.

During the surgical process, it is required to obtain the position of the specific object in real time. For example, the image of the surgical device may be obtained by the image obtaining device, and it may be judged whether the current position of the surgical device is within the preset recognition range. If the position of the surgical device or the operating angle deviates, prompts are provided to the user to assist the user in performing the surgical operation.

Figure 4:
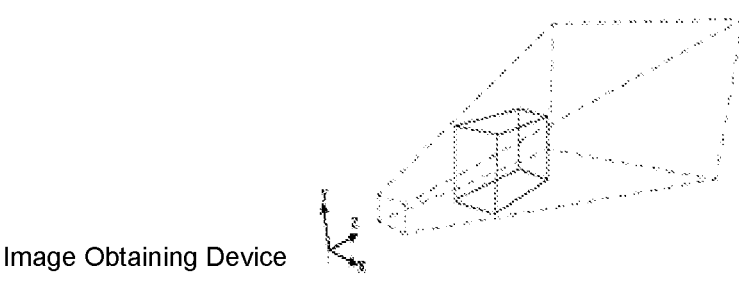
FIG. 4 is a diagram of a preset recognition range in the dynamic position recognition and prompt method of the present invention.

It is to be noted that the preset recognition range is a spatial shape range radially increasing along the shooting direction of the image obtaining device, which may be a spatial range constructed by a conical structure. For example, it is may be a spatial shape, with the image obtaining device as a proximal end, radially increasing along the image obtaining direction toward the distal end. As shown in FIG. 4, the end where the image obtaining device is located is the proximal end, the structure of which is configured to be a rectangular structure, and the end away from the image obtaining device is the distal end, the structure of which is a rectangular structure with the area being greater than that of the proximal end. The distal end structure and the proximal end structure are connected to construct a closed three-dimensional space, and form a preset recognition area. In FIG. 4, the preset recognition area is the range shown by the dashed line, and the optimal recognition range is the range shown by the solid line. When the surgical device has not entered into the preset recognition area, the prompt is provided to the user in time, so that the user may move the surgical device to reach the preset recognition area. Further, the prompt may be provided to user that it has been within the optimal recognition range.

In one embodiment, the determined shooting recognition range in front of the image obtaining device may comprise:

Unrecognizable range: an imaging area of the image obtaining device which is completely unsupported by the algorithm;

Transitional area: an area in which a pattern can be recognized and tracked by the algorithm, but is not within the optimal range;

Optimal area: an area with recognition accuracy being ensured, which is supported by the algorithm;

Transitional angle: an angle in which a pattern can be recognized and tracked by algorithms, but is not within the optimal angle;

Optimal angle: an angle with recognition accuracy being ensured, which is supported by the algorithm.

Depending on the areas, different prompts may be made.

Further preferably, the preset recognition range is an operable implementation range in the scene. However, under some special requirements, more accurate positioning and recognition are required. An optimal recognition range is set in the present invention. The optimal recognition range is within the preset recognition range, generally in the center of the preset recognition range, and the preset recognition range is greater than the optimal recognition range. The optimal recognition range comprises: an optimal recognition range preset based on the user's instructions and/or a historical optimal recognition range obtained based on data statistics.

Figure 5:
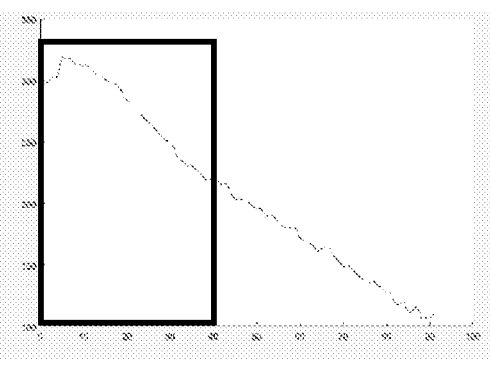
FIG. 5 is a diagram of an optimal recognition distance range in the dynamic position recognition and prompt method of the present invention.

As shown in FIG. 5, accuracy of feature recognition for the specific object based on the image is statistically analyzed, wherein the horizontal coordinate refers to the distance between the specific object and the image obtaining device, and the vertical coordinate refers to the number of recognizable points. The selected area refers to a selected optimal recognition distance, and based on the projection outline formed by the whole recognizable pattern within the optimal recognition angle and at the optimal recognition angle, an area prompt for the optimal recognition range in the field of view is formed.

Figure 6:
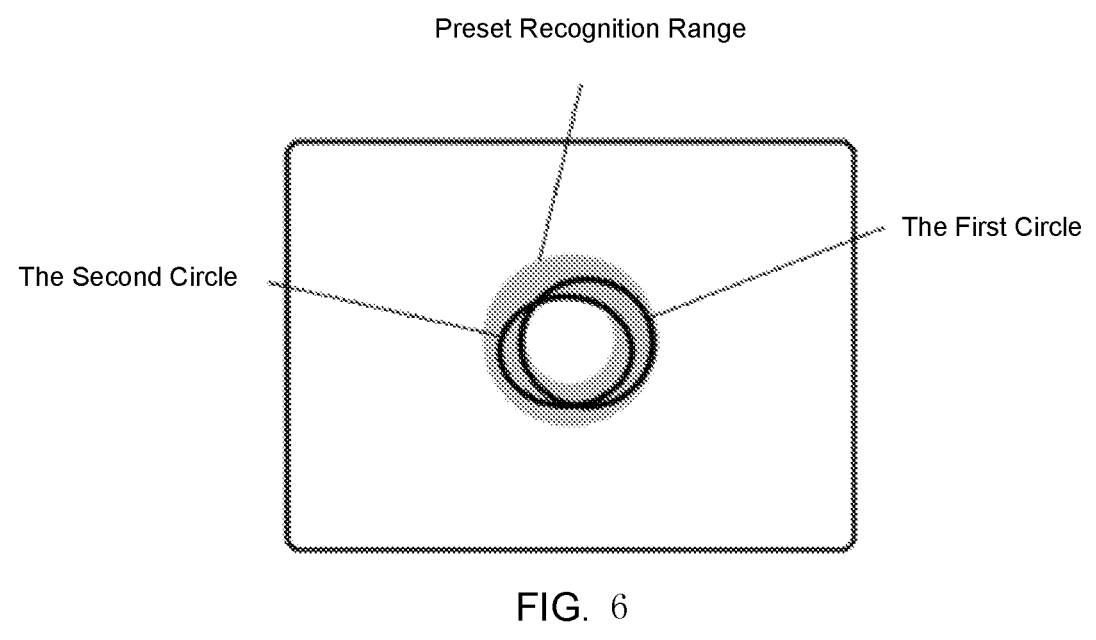

As shown in FIG. 6, the optimal recognition range may be set based on an angle. Taking the surgical device in FIG. 3 as an example, if the surgical device is viewed orthogonally from the handle end and the edge of the bowl-shaped structure on the handle is projected, when the surgical device is at any recognizable angle and within the recognizable range of the image obtaining device, a collection of all the positions of the projection pattern of the boundary of the bowl of the device forms the preset recognition range. During the surgical process, the preset recognition range is displayed in the corresponding positon of the real scene in the augmented reality manner. As long as the edge of the bowl-shaped structure on the handle is within the preset recognition range when the surgical device is manipulated by the user, it means that it is located in the recognizable range, making it easy for the operator to promptly adjust the position thereof.

It can be understood that when the orientation of the surgical device is the same as the shooting direction of the image obtaining device, the edge of the bowl-shaped structure on the handle is projected to form a standard circle, such as the first circle in FIG. 6, and at this time, the movement of the surgical device along the shooting direction may result in a change in the size of the projected circle, and as long as the edge of the bowl-shaped structure of the surgical device is still in the preset recognition range displayed in the augmented reality mode, the surgical device can be recognized. If the surgical device is deflected by a certain angle and the profile of its edge becomes an ellipse, such as the second circle in FIG. 6, the surgical device can still be recognized as long as the deflection angle is within an acceptable range, i.e., the edge of the bowl-shaped structure of the surgical device is still within the preset recognition range displayed in the augmented reality manner.

The shown optimal recognition range may be dynamically adjusted according to the accuracy requirement or operation requirement; when the specific object is in a fine operation requirement, the optimal recognition range contracts; when the specific object is in a rough operation requirement, the optimal recognition range expands. For example, when the puncture needle is outside the patient's body, a narrow recognition range may be used for obtaining a more accurate spatial positioning, while when the puncture needle is inserted into the human body, the recognizable range may be appropriately widened to help the surgeons complete the surgical steps more quickly and reduce surgical risks. In combination with the second point above, when the puncture needle is outside the patient's body, only if it is within the optimal area and at the optimal angle, it can be considered that the current positional relationship between the puncture needle and the image obtaining device is in a preset positional relationship interval; and when the puncture needle enters the human body, if it is within the transitional area or at the transitional angle, it can also be considered to be in the preset recognition positional relationship. The optimal recognition range may also be dynamically adjusted according to the handheld stability of the operator. In one embodiment, the augmented reality navigation device may record historical operation information of the users who use different user (doctor) account, and based on the data statistics, the optimal recognition interval range is larger for the users with good history records, as this group of users relies less on the navigation accuracy, but the optimal recognition interval is smaller for the users with poorer stability showed by the history record.

In addition, the preset recognition range may be divided into multiple prompt levels according to the requirements and the levels of the surgeries, so that when the specific object is at a different position, a reminder and prompt of a different level is made to help the user carry out the surgical operations.

In S4, the prompt message is displayed in the augmented reality manner to prompt the user to adjust the specific object to be within the preset recognition range if the current position of the specific object is not within the preset recognition range.

Wherein displaying the prompt message in the augmented reality manner to prompt the user to adjust the specific object to be within the preset recognition range comprises: the prompt message comprising at least the positional relationship between the specific object and the preset recognition range to prompt the user to adjust the position of the specific object or the image obtaining device. Wherein, the prompt message is one or a combination of more of text, color, pattern, animation superimposed on the current scene in the augmented reality manner. Since a quiet environment is required during the surgery, a voice mode is not used in the present invention for the user's convenience. However, the voice mode may be used for prompting in different scenes. In augmented reality, with the text, the color, or the pattern displayed to the user, the user can get the prompt message after he sees it, and in turn move the surgical device used during the surgery or move the display device.

In addition, after the prompt is made, it allows to assist the user to move the position of the specific object or the image obtaining device, so that the current position of the specific object is enabled to be within the preset recognition range The position movement message comprises one or a combination of more of text, auxiliary line, or animation superimposed on the current scene in the augmented reality manner. The user may move the specific object or the image obtaining device with the aid of the prompt of the text, the auxiliary line or the animation, so that the specific object or the image obtaining device can quickly and accurately reach the optimal position. The optimal recognition range may be dynamically adjusted according to different surgical phases, the existing stability records of the specific object and the existing surgical records of the operator. Voice may also be used to prompt the position movement.

According to the dynamic position recognition and prompt method of the present invention, laboratory measurements of the specific object are carried out to define its three-dimensional optimal recognition range and three-dimensional optimal recognition angle relative to the image obtaining device according to the expected positioning accuracy. By calculating in real time the relative relationship between the current position of the specific object and the optimal recognition area, the prompt is provided to the operator by means of color, graphic, animation, and the like as to whether or not the recognition position should be adjusted at present, which enables the specific object to be adjusted to an appropriate position, and in turn to continue the subsequent surgical steps.

For those skilled in the art, it is understandable that the above specific embodiments are only those preferred solutions of the present invention, thus the improvements and changes that may be made by those skilled in the art to certain parts of the present invention still reflect the principle of the present invention, and achieve the purpose of the present invention, thus all within the protection scope of the present invention.

What is claimed is:

1. A dynamic position recognition and prompt system, characterized in that it comprises: a recognition module, a judgment module, and a prompt module; wherein the recognition module is used to obtain a current scene image via an image obtaining device, and recognize a current position of a specific object in the current scene image;

the judgment module is used to judge whether the current position of the specific object is within a preset recognition range;

the prompt module is used to display a prompt message in an augmented reality manner to prompt a user to adjust the specific object to be within the preset recognition range if the current position of the specific object is not within the preset recognition range;

wherein the judgment module comprises an optimal recognition range judgment sub-module for judging whether the current position of the specific object is within an optimal recognition range of the image obtaining device; the optimal recognition range being within the preset recognition range, the preset recognition range being greater than the optimal recognition range; and wherein the optimal recognition range is adjusted according to the operation requirement, when the specific object is in a fine operation requirement, the optimal recognition range contracts; when the specific object is in a rough operation requirement, the optimal recognition range expands.

2. The dynamic position recognition and prompt system according to claim 1, characterized in that the preset recognition range is a recognition distance range and/or a recognition angle range which is preset; the judgment module is specifically used to judge whether the specific object is within the recognition distance range; and/or to judge whether the specific object is within the recognition angle range.

3. The dynamic position recognition and prompt system according to claim 1, characterized in that the preset recognition range is set to be a spatial shape range radially increasing along a shooting direction of the image obtaining device.

4. The dynamic position recognition and prompt system according to claim 1, characterized in that the judgment module further comprises a recognition range setting module for setting the preset recognition range and/or the optimal recognition range.

5. The dynamic position recognition and prompt system according to claim 4, characterized in that the optimal recognition range comprises: an optimal recognition range preset based on the user's instruction and/or a historical optimal recognition range obtained based on data statistics.

6. The dynamic position recognition and prompt system according to claim 1, characterized in that the prompt message comprises at least a positional relationship between the specific object and the preset recognition range to prompt the user to adjust the position of the specific object or the image obtaining device.

7. The dynamic position recognition and prompt system according to claim 1, characterized in that the prompt message is one or a combination of more of text, color, pattern, and animation superimposed on the current scene in the augmented reality manner.

8. The dynamic position recognition and prompt system according to claim 1, characterized in that the prompt module further comprises a movement prompt sub-module for displaying a position movement message to prompt the user to move the position of the specific object or the image obtaining device, so that the specific object is enabled to be within the preset recognition range; the position movement message comprising: one or a combination of more of text, auxiliary line, or animation superimposed on the current scene in the augmented reality manner.

9. The dynamic position recognition and prompt system according to claim 1, characterized in that the specific object is a specific object with a recognizable feature.

10. A dynamic position recognition and prompt method, characterized in that it comprises:

obtaining a current scene image;

recognizing a current position of a specific object in the current scene image;

judging whether the current position of the specific object is within a preset recognition range;

displaying a prompt message in an augmented reality manner to prompt a user to adjust the specific object to be within the preset recognition range if the current position of the specific object is not within the preset recognition range;

wherein the method further comprises judging whether the current position of the specific object is within an optimal recognition range of the image obtaining device; the optimal recognition range being within the preset recognition range, the preset recognition range being greater than the optimal recognition range; and wherein the optimal recognition range is adjusted according to the operation requirement, when the specific object is in a fine operation requirement, the optimal recognition range contracts; when the specific object is in a rough operation requirement, the optimal recognition range expands.

11. The dynamic position recognition and prompt method according to claim 10, characterized in that the preset recognition range is a recognition distant range and/or a recognition angle range which is preset.

* * * * *